(12) United States Patent
McLeod

(10) Patent No.: US 10,038,408 B2
(45) Date of Patent: Jul. 31, 2018

(54) PSEUDO-RANDOM CHOPPER AMPLIFIER

(71) Applicant: Cactus Semiconductor, Inc., Chandler, AZ (US)

(72) Inventor: Scott Cameron McLeod, Oro Valley, AZ (US)

(73) Assignee: Cactus Semiconductor, Inc., Chandler, AZ (US)

(*) Notice: Subject to any disclaimer, the term of this patent is extended or adjusted under 35 U.S.C. 154(b) by 0 days.

(21) Appl. No.: 15/194,229

(22) Filed: Jun. 27, 2016

(65) Prior Publication Data

US 2016/0380598 A1 Dec. 29, 2016

Related U.S. Application Data

(60) Provisional application No. 62/185,272, filed on Jun. 26, 2015.

(51) Int. Cl.
| | | |
|---|---|---|
| *A61B 5/00* | (2006.01) |
| *H03F 1/26* | (2006.01) |
| *H03F 3/393* | (2006.01) |
| *H03F 3/45* | (2006.01) |
| *A61B 5/0402* | (2006.01) |
| *A61B 5/0488* | (2006.01) |
| *A61B 5/0476* | (2006.01) |

(52) U.S. Cl.
CPC ............ *H03F 1/26* (2013.01); *A61B 5/0402* (2013.01); *A61B 5/0476* (2013.01); *A61B 5/0488* (2013.01); *A61B 5/7203* (2013.01); *A61B 5/7228* (2013.01); *H03F 3/393* (2013.01); *H03F 3/45179* (2013.01); *H03F 3/45475* (2013.01); *H03F 2200/261* (2013.01); *H03F 2200/271* (2013.01); *H03F 2203/45288* (2013.01)

(58) Field of Classification Search
CPC ........ H03F 1/26; H03F 3/393; H03F 3/45179; H03F 3/45475; A61B 5/0402; A61B 5/0476; A61B 5/0488; A61B 5/7203; A61B 5/7228

See application file for complete search history.

(56) References Cited

U.S. PATENT DOCUMENTS

| | | | |
|---|---|---|---|
| 9,444,414 B2 * | 9/2016 | Peluso | H03F 3/005 |
| 2011/0304400 A1 * | 12/2011 | Stanley | H03F 1/26 330/295 |
| 2016/0261244 A1 * | 9/2016 | Huang | H03F 3/387 |

* cited by examiner

*Primary Examiner* — Scott Getzow
(74) *Attorney, Agent, or Firm* — Ballard Spahr LLP

(57) ABSTRACT

A chopper stabilized amplifier that utilizes a multi-frequency chopping signal to reduce chopping artifacts. By utilizing a multi-frequency chopping signal, the amplifier DC offset and flicker noise are translated to the higher chopping frequencies but are also smeared, or spread out in frequency and consequently lowered in amplitude. This lower amplitude signal allows for less stringent filtering requirements.

20 Claims, 4 Drawing Sheets

Input Signal Bandwidth

Amplifier Noise

Chopper Signal

Chopped Input Signal &
Amplifier Noise

Chopped Amplifier Noise

Restored Input Signal &
Chopped Amplifier Noise

Chopped Amplifier

Non-Overlapping Signals

Multi-Frequency
Chopping Signals

Input Signal Bandwidth

Amplifier Noise

Chopper Signal

Chopped Input Signal &
Amplifier Noise

Chopped Amplifier Noise

Restored Input Signal &
Chopped Amplifier Noise

PSEUDO-RANDOM CHOPPER AMPLIFIER

RELATED APPLICATION

This non-provisional patent application claims priority to provisional U.S. Patent Application No. 62/185,272, entitled "Pseudo-Random Chopper Amplifier," filed on Jun. 26, 2015 and incorporated herein by reference in its entirety.

BACKGROUND

Field of the Disclosure

Aspects of the disclosure relate in general to amplifiers. Aspects include a chopper stabilized amplifier that utilizes a multi-frequency chopping signal to reduce chopping artifacts.

Description of the Related Art

Instrumentation amplifiers are used to accurately measure a variety of test and measurement signals. A medical instrumentation amplifier, for example, may be configured to measure physiological signals, such as electrocardiogram (ECG), electromyogram (EMG), electroencephalogram (EEG), pressure, impedance, and motion signals. Typically, instrumentation amplifiers are constructed as differential amplifiers exhibiting low offset, low drift, low noise, high common mode rejection, high loop gain, and high input impedance. In many cases, instrumentation amplifiers may require careful matching and trimming of circuit components to achieve a high degree of accuracy.

An instrumentation amplifier may be constructed with a discrete time switched capacitor architecture that obtains discrete signal samples. However, a discrete time architecture can produce undesirable aliasing of noise and signals, undermining the accuracy of measurement signals. Alternatively, an instrumentation amplifier may employ a chopper stabilized architecture in which a chopper circuit up-modulates a measurement signal into a higher frequency band to minimize amplifier noise and offset errors. A chopper-stabilized architecture may have a limited bandwidth, however, producing a large ripple in the passband. The ripple may make implementation of chopper-stabilized designs difficult in low power applications.

FIGS. 1-6 are graphs depicting signals for a type of chopping amplifiers of the prior art. FIG. 1 illustrates the frequency components of an input signal with a single-sided bandwidth. FIG. 2 depicts the undesirable offset and noise components of an amplifier. The frequency components include flicker noise and thermal noise. FIG. 3 illustrates the single frequency component of the modulated signal. FIG. 4 shows the double-sided bandwidth of the chopped input signal and amplifier noise. FIG. 5 illustrates chopped amplifier noise and offset. FIG. 6 illustrates a restored input signal and chopped amplifier noise.

SUMMARY

Embodiments include an electrical circuit or device with a chopper-stabilized amplifier that utilizes a multi-frequency chopping signal to reduce chopping artifacts.

An apparatus embodiment comprises a first modulator, a differential amplifier, a first input capacitor, a second input capacitor, a first output capacitor, a first switched feedback path, and a second switched feedback path. The first modulator is configured to modulate the amplitude of a differential input signal at multiple frequencies using a plurality of first modulator switches driven by non-overlapping signals, φ1 and φ2. The first modulator produces a differential modulated signal. The differential amplifier has a positive input, a negative input, a positive output, and a negative output. The differential amplifier is configured to amplify the differential modulated signal received at the positive input and negative input to produce a differential amplified signal. The differential amplifier signal is output by the differential amplifier at the positive output and the negative output. The first input capacitor is coupled between a first output of the first modulator and the positive input of the differential amplifier. The second input capacitor is coupled between a second output of the first modulator and the negative input of the differential amplifier. The first output capacitor is coupled between the positive output and the negative output of the differential amplifier. The first switched feedback path is coupled between the positive output and the node between the first input capacitor and the positive input of the amplifier. The first switched feedback path includes a first feedback capacitor in parallel with two first P-type Metal Oxide Semiconductor field effect transistors (MOSFET) connected drain-to-source. The first switched feedback path is switched by the non-overlapping signals, φ1 and φ2. The second switched feedback path is coupled between the negative output and the node between the second input capacitor and the negative input of the amplifier. The second feedback path includes a second feedback capacitor in parallel with two second P-type MOSFETs connected drain-to-source. The second switched feedback path is switched by the non-overlapping signals, φ1 and φ2.

In some embodiments, the apparatus further comprises a physiological sensor that generates the differential input signal, wherein the differential input signal is indicative of a physiological condition, and wherein the physiological sensor includes one of an accelerometer, a pressure sensor, and a voltage sensor.

In some other embodiments, the apparatus further comprises a physiological sensor that generates the differential input signal, wherein the differential input signal is indicative of a physiological condition, and wherein the physiological sensor includes one of an electrocardiogram (ECG), electromyogram (EMG), or electroencephalogram (EEG) sensor.

DETAILED DESCRIPTION

One aspect of the disclosure includes the realization that conventional amplifiers use a single "selected" frequency for the chopping signal which results in higher amplitude chopping artifacts.

Accordingly, another aspect of the disclosure includes a chopper stabilized amplifier that utilizes a multi-frequency chopping signal to reduce chopping artifacts such as low frequency 1/f ("flicker") noise. By utilizing a multi-frequency chopping signal, the amplifier DC offset and flicker noise are translated to the higher chopping frequencies but are also smeared, or spread out in frequency and consequently lowered in amplitude. This lower amplitude signal allows for less stringent filtering requirements.

Figure 1:
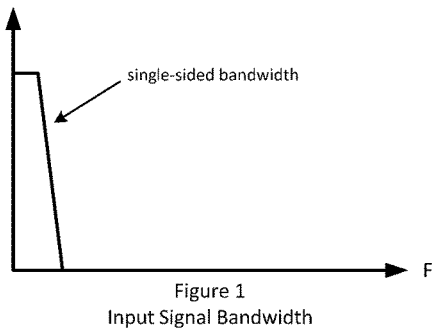
FIGS. 1-6 depict signals for a type of chopping amplifiers of the prior art.
Figure 2:
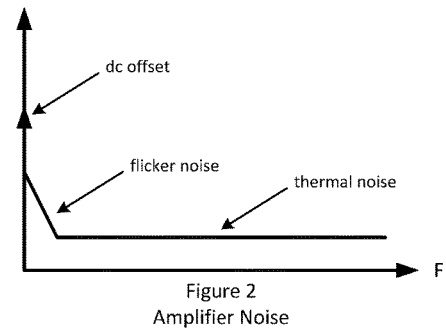
Figure 3:
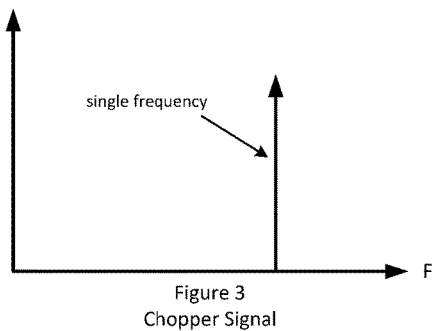
Figure 4:
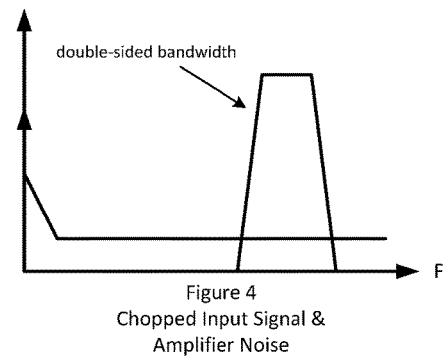
Figure 5:
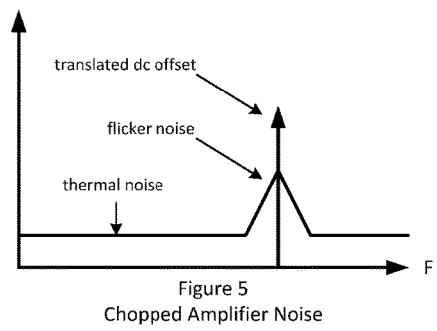
Figure 6:
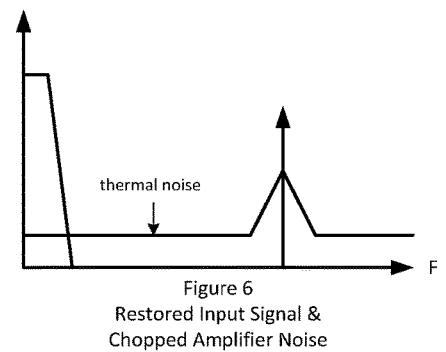
Figure 7:
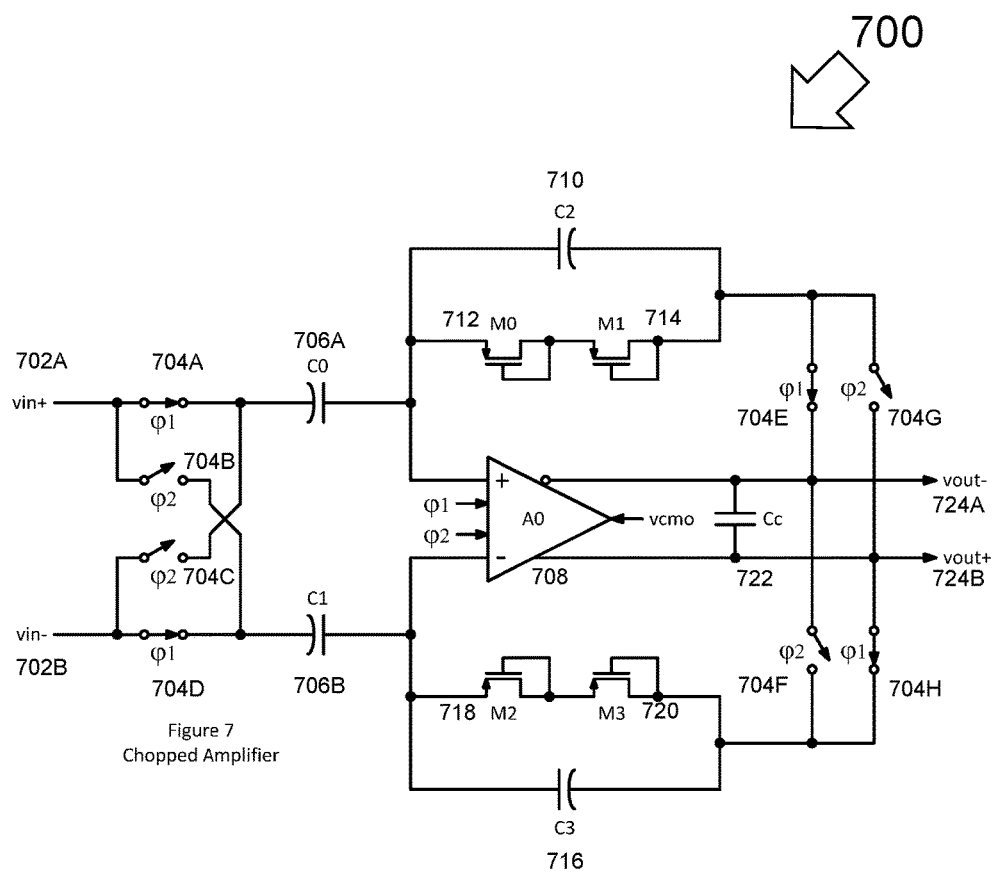
FIG. 7 is a schematic of an embodiment chopper amplifier, suitable for medical sensing applications, that uses a multi-frequency chopping signal.

An FIG. 7 is a schematic of an embodiment chopper amplifier 700, suitable for medical sensing applications, which uses a multi-frequency chopping signal, constructed and operative in accordance with an embodiment of the present disclosure. The chopper amplifier 700 may be connected to a sensor which generates a differential voltage provided to chopper amplifier inputs vin+ 702A and vin− 702B (collectively, "inputs 702"). It is understood by those familiar with the art that the sensor may be a physiological sensor that translates biophysical signals to a differential electrical voltage across inputs 702. Physiological signals may include electrocardiogram (ECG), electromyogram (EMG), electroencephalogram (EEG), pressure, impedance, and motion signals. Consequently, the sensor may be an accelerometer, a pressure sensor, a force sensor, a gyroscope, a humidity sensor.

Inputs 702A and 702B are connected to capacitors 706A and 706B (collectively, "capacitors 706") through switches 704A-D (collectively, "switches 704"), respectively. The capacitors 706A-B have capacitances of C0 and C1, respectively. Switches 704 are driven by non-overlapping signals, φ1 and φ2 and depicted in FIG. 8.

Figure 8:
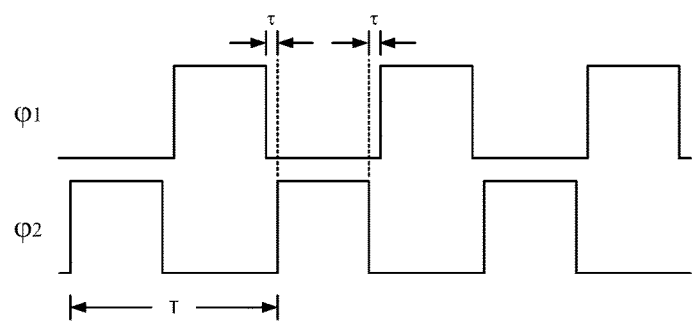
FIG. 8 shows the characteristics of non-overlapping signals φ1 and φ2 used by an embodiment chopper amplifier.

As shown in FIG. 8, non-overlapping signals φ1 and φ2 have a period of T.

Capacitors 706 are coupled at one end to a corresponding one of switches 704 and to a corresponding input of amplifier 708 at the other end. In particular, capacitor 706A is coupled to the positive input of amplifier 708, and capacitor 706B is coupled to the negative input of amplifier 708, providing a differential input.

Figure 9:
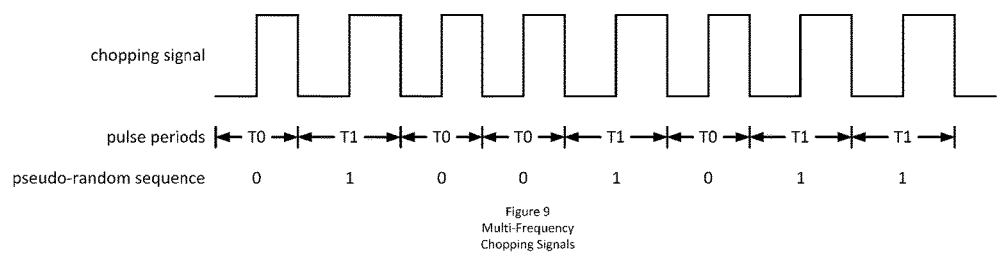
FIG. 9 depicts one implementation of a multi-frequency chopping signal.

Amplifier 708 may be a transconductance stage with differential input and differential output current. Amplifier 708 is chopped internally as indicated by the φ1 and φ2 inputs. An example resultant chopping signal is shown in FIG. 9.

In FIG. 7, sensor, switches 704A-D, and capacitors 706A-B form a front end of amplifier 708. In particular, the front end operates as a continuous time switched capacitor network. Switches 704A-D toggle between an open state and a closed state in which inputs 702A-B are coupled to capacitors 706A-B at a clock frequency to modulate (chop) the output of sensor at the chopping frequency. The output of the sensor may be a low frequency signal within a range of approximately 0 Hz to approximately 100 Hz. The chopping frequency may be within a range of approximately 4 kHz to approximately 10 kHz. As a result, the low frequency sensor output is chopped to the higher chop frequency band.

Switches 704A-D toggle in-phase with one another to provide a differential input signal to amplifier 708. During a first phase of signal φ1, switches 704A connect sensor output 702A to capacitor 706A and switch 704B remains open. At the same time, switch 704D connects sensor output 702B to capacitor 706B. As signal φ2 is in opposite phase of signal φ1, both switch 704B and 704C are open at this time.

During a second phase of signal φ1, signal φ2 is in opposite phase and switches 704A-D change state such that switch 704B couples port 702A to capacitor 706B and switch 704C couples port 702B to capacitor 706A. Both switch 704A and 704D are open at this time.

Switches 704A-D synchronously alternate between the first and second phases to modulate the differential voltage at inputs 702 at the chopping frequency. The resulting chopped differential signal is applied across capacitors 706, which couple the differential signal across the inputs of amplifier 708.

Amplifier 708 may produce noise and offset in the differential signal applied to its inputs. For this reason, the differential input signal is chopped via switches 704A-D and capacitors 706A-B to place the signal of interest in a different frequency band from the noise and offset.

Then, amplifier 708 chops the amplified signal to demodulate the signal of interest down to baseband while modulating the noise and offset up to the chop frequency band. In this manner, chopper amplifier 700 maintains substantial separation between the noise and offset and the signal of interest. The output from amplifier 708 is a differential voltage vout− 724A and vout+ 724B, collectively "differential voltage 724." A compensation capacitor (Cc) 722 sets the amplifier output bandwidth.

Amplifier 708 receives feedback from the differential voltage 724 switched by non-overlapping signals, φ1 and φ2 via switches 704E-H. Switches 704E and 704H are controlled by signal φ1, while switches 704F and 704G are controlled by signal φ2.

As shown in FIG. 7, the feedback path may include two feedback path branches connected by the switches 704E-H as described above. The top feedback path branch passes the vout− 724A or vout+ 724B output of amplifier 708 to positive input terminal of amplifier 708 via two P-type Metal Oxide Semiconductor field effect transistors (MOSFET) 712 and 714 connected drain-to-source in parallel with a capacitor 710 (having a capacitance C2). The bottom feedback path branch of the feedback path connects the vout+ 724B or vout− 724A output of amplifier 708 to negative input terminal of amplifier 708 via two P-type Metal Oxide Semiconductor field effect transistors (MOSFET) 718 and 720 connected drain-to-source in parallel with a capacitor 716 (having a capacitance C3).

The feedback paths are used to create a low frequency, high pass filter.

The gain of the circuit is equal to C0/C2=C1/C3.

Figure 10:
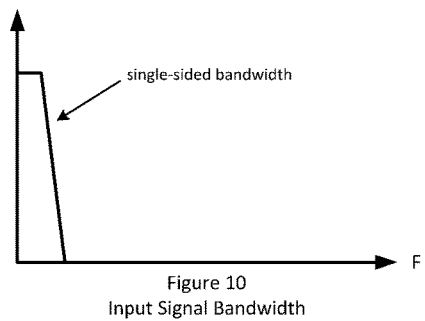
FIGS. 10-15 depict signals for a multi-frequency chopping amplifier embodiment.
Figure 11:
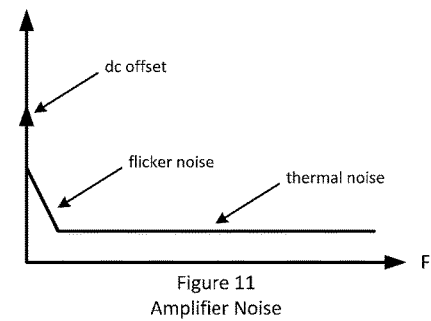
Figure 12:
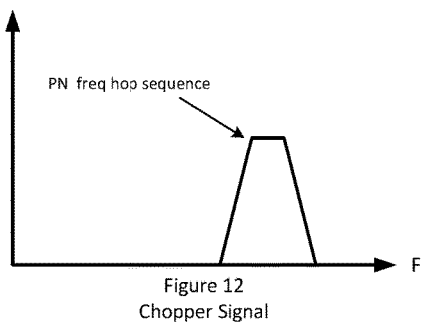
Figure 13:
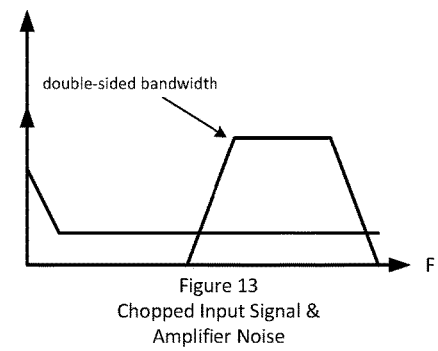
Figure 14:
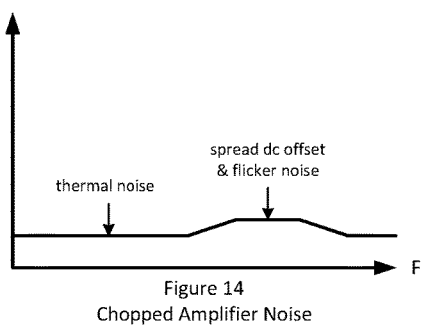
Figure 15:
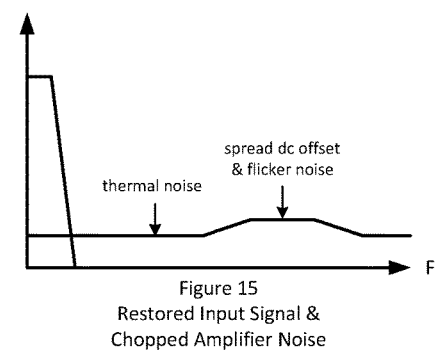

FIGS. 10-15 depict signals for a multi-frequency chopping amplifier embodiment 700, constructed and operative in accordance with an embodiment of the present disclosure. FIG. 10 illustrates the frequency components of an input signal with a single-sided bandwidth. FIG. 11 depicts the undesirable offset and noise components of an amplifier. The frequency components include flicker noise and thermal noise. FIG. 12 illustrates a multi-frequency components of the modulated chopper signal. FIG. 13 shows the double-sided bandwidth of the chopped input signal and amplifier noise. FIG. 14 illustrates chopped amplifier noise where the amplifier DC offset and flicker noise are translated to the higher chopping frequencies but are also smeared, or spread out in frequency and consequently lowered in amplitude. FIG. 15 illustrates a restored input signal and chopped amplifier noise spread out in frequency and lowered in amplitude.

The previous description of the embodiments is provided to enable any person skilled in the art to practice the disclosure. The various modifications to these embodiments will be readily apparent to those skilled in the art, and the generic principles defined herein may be applied to other embodiments without the use of inventive faculty. Thus, the present disclosure is not intended to be limited to the embodiments shown herein, but is to be accorded the widest scope consistent with the principles and novel features disclosed herein.

What is claimed is:

1. An apparatus comprising:
   a first modulator comprising a plurality of modulator switches driven by non-overlapping signals and a plurality of outputs, configured to:
      modulate, via the plurality of modulator switches, an amplitude of a differential input signal at multiple frequencies; and
      generate a differential modulated signal;
   a differential amplifier comprising a positive input, a negative input, a positive output, and a negative output, configured to:
      receive, at the positive input and the negative input, the differential modulated signal;
      amplify the differential modulated signal;
      generate a differential amplified signal; and
      output, at the positive output and the negative output, the differential amplified signal;
   a first input capacitor coupled between a first output of the plurality of outputs of the first modulator and the positive input of the differential amplifier;
   a second input capacitor coupled between a second output of the plurality of outputs of the first modulator and the negative input of the differential amplifier;
   an output capacitor coupled between the positive output of the differential amplifier and the negative output of the differential amplifier;
   a first switched feedback path coupled between the positive output of a first node between the first input capacitor and the positive input of the differential amplifier, wherein the first switched feedback path comprises a first feedback capacitor in parallel with a first pair of transistors, wherein the first switched feedback path is switched by the non-overlapping signals; and
   a second switched feedback path coupled between the negative output of a second node between the second input capacitor and the negative input of the differential amplifier, wherein the second feedback path comprises a second feedback capacitor in parallel with a second pair of transistors, wherein the second switched feedback path is switched by the non-overlapping signals.

2. The apparatus of claim 1, further comprising a physiological sensor, wherein the physiological sensor is configured to generate the differential input signal, wherein the differential input signal indicates a physiological condition.

3. The apparatus of claim 2, wherein the physiological sensor comprises one or more of an electrocardiogram (ECG), an electromyogram (EMG), or an electroencephalogram (EEG) sensor.

4. The apparatus of claim 2, wherein the physiological sensor comprises one or more of an accelerometer, a pressure sensor, or a voltage sensor.

5. The apparatus of claim 2, wherein the physiological sensor comprises a chopping frequency between 4 kilohertz and 10 kilohertz.

6. The apparatus of claim 1, wherein the first pair of transistors are P-type Metal Oxide Semiconductor field effect transistors (MOSFET).

7. The apparatus of claim 1, wherein each transistor of the first pair of transistors comprises a drain-to-source connection.

8. The apparatus of claim 1, wherein the second pair of transistors are P-type Metal Oxide Semiconductor field effect transistors (MOSFET).

9. The apparatus of claim 1, wherein each transistor of the second pair of transistors comprises a drain-to-source connection.

10. The apparatus of claim 1, wherein the differential input signal comprises a frequency between 0 hertz and 100 hertz.

11. The apparatus of claim 1, wherein the differential input signal comprises a plurality of non-uniform pulse periods.

12. The apparatus of claim 1, wherein each modulator switch of the plurality of modulator switches is in phase with the plurality of modulator switches.

13. The apparatus of claim 1, wherein the plurality of modulator switches switch according to a clock signal.

14. The apparatus of claim 1, wherein a gain of the apparatus is equal to a capacitance of the first input capacitor divided by a capacitance of the first feedback capacitor.

15. The apparatus of claim 1, wherein a gain of the apparatus is equal to a capacitance of the second input capacitor divided by a capacitance of the second feedback capacitor.

16. The apparatus of claim 1, wherein the first switched feedback path is configured as a high-pass signal filter.

17. The apparatus of claim 1, wherein the second switched feedback path is configured as a high-pass signal filter.

18. The apparatus of claim 1, wherein a period associated with a first signal of the non-overlapping signals is equal to a period associated with a second signal of the non-overlapping signals.

19. The apparatus of claim 1, wherein the non-overlapping signals are square wave signals.

20. The apparatus of claim 1, wherein an amount of signal noise associated with one or more of the non-overlapping signals is more than an amount of signal noise associated with the differential amplified signal.

* * * * *